(12) United States Patent
Macchi

(10) Patent No.: US 7,074,037 B2
(45) Date of Patent: Jul. 11, 2006

(54) BRACKET FOR ORTHODONTIC APPLIANCES

(76) Inventor: Aldo Macchi, Via G. Piatti, 9, 21100 Varese (IT)

(*) Notice: Subject to any disclaimer, the term of this patent is extended or adjusted under 35 U.S.C. 154(b) by 16 days.

(21) Appl. No.: 10/898,760

(22) Filed: Jul. 26, 2004

(65) Prior Publication Data
US 2006/0019212 A1    Jan. 26, 2006

(51) Int. Cl.
*A61C 7/00* (2006.01)
(52) U.S. Cl. .................................................. 433/10
(58) Field of Classification Search .................. 433/8, 433/9, 10, 11, 13, 14
See application file for complete search history.

(56) References Cited

U.S. PATENT DOCUMENTS

| 4,582,487 | A | | 4/1986 | Creekmore |
| 4,655,708 | A | | 4/1987 | Fujita |
| 4,712,999 | A | * | 12/1987 | Rosenberg ................. 433/8 |
| 5,123,838 | A | * | 6/1992 | Cannon ...................... 433/14 |
| 5,362,233 | A | * | 11/1994 | Thompson .................. 433/9 |
| 5,474,444 | A | | 12/1995 | Wildman |
| RE35,863 | E | * | 7/1998 | Sachdeva et al. .......... 433/8 |
| 5,947,723 | A | | 9/1999 | Mottate et al. |
| 6,632,088 | B1 | * | 10/2003 | Voudouris .................. 433/18 |

* cited by examiner

Primary Examiner—Melba N. Bumgarner
(74) Attorney, Agent, or Firm—Pearne & Gordon LLP

(57) ABSTRACT

A bracket for orthodontic appliances comprises a plate-like base (10), first support means (20) mounted on the base (10) and defining a first housing (25) for a first archwire (30), and second support means (40) mounted on the base (10) and defining a second housing (45) for a second archwire (31). The bracket (1) further has a concave portion (64) defining an auxiliary housing for a pin (32) positioned transversely of the first and second archwires (30, 31).

17 Claims, 5 Drawing Sheets

BRACKET FOR ORTHODONTIC APPLIANCES

FIELD AND BACKGROUND OF THE INVENTION

The present invention relates to a bracket for orthodontic appliances.

It is known that orthodontic appliances utilized for correcting the position and/or orientation of the teeth in a patient generally consist of an archwire made of a metal material and a plurality of brackets. Each bracket has a suitable housing seat on one side for engagement of the archwire, while on the opposite side said bracket is secured to a tooth; in this way, by arranging the archwire following predetermined conformations, a corrective action can be exerted on one or more teeth so as to improve position and inclination of same.

The presently-used brackets comprise a substantially rectangular base on a face of which a pair of hooks is welded; the hooks engage the archwire of circular section, whereas the opposite base face is fastened to the tooth generally through suitable composite materials.

By means of brackets as briefly described above, a rotation around the vertical axis of the tooth can be applied to the tooth itself and/or also a rotation around a horizontal axis oriented transversely of the tooth from the inside to the outside of the oral cavity (in the vestibulum-lingualis direction).

Rotations around the meso-distal axis of the tooth can be also applied, i.e. rotations around a horizontal axis substantially orthogonal to the vestibulum-lingualis axis; these rotations (also referred to as "torque") are carried out through use of an archwire or sectionals of rectangular section.

The brackets used in this case are provided with a groove having a shape suitably conforming to that of the archwire which is inserted thereinto on accomplishment of the orthodontic appliance.

However, through a single archwire of rectangular section only forces of limited intensity can be applied to the tooth; in particular the imposed torque for a rotation around the meso-distal axis (i.e. for a rotation in the vestibulum-lingualis direction) is limited by the sizes of the transverse section of the archwire itself. Therefore, for increasing the intensity of this torque (for teeth requiring important torque corrections, for example), the sizes of the archwire section should be correspondingly increased, which will make said archwire practically unusable.

SUMMARY OF THE INVENTION

Accordingly, the present invention aims at providing a bracket for orthodontic appliances allowing all the correction forces applied to a tooth to be controlled in a precise and flexible manner.

Another aim of the invention is to make available a bracket for orthodontic appliances allowing a torque of high intensity to be applied without increasing the sizes of the archwire used.

A further aim of the present invention is to provide a bracket for orthodontic appliances capable of ensuring a strong and reliable link between the support means housing the archwire being used and the base of the bracket itself.

Another aim of the present invention is to provide a bracket for orthodontic appliances ensuring an easy insertion of the archwire into the corresponding seat, without any ligature for keeping it in place being required, which will facilitate the operator's work.

A still further aim of the present invention is to provide a bracket for orthodontic appliances enabling corrections and finishing operations to be carried out on the appliance arrangement even after said appliance has been installed in the patient's oral cavity.

These and further aims are substantially achieved by the bracket for orthodontic appliances as disclosed in the appended claims.

BRIEF DESCRIPTION OF THE DRAWINGS

Further features and advantages will become more apparent from the detailed description of a preferred but non-limiting embodiment of a bracket for orthodontic appliances in accordance with the present invention. This description will be taken hereinafter with reference to the accompanying drawings, given by way of non-limiting example, in which.

DESCRIPTION OF THE PREFERRED EMBODIMENT

Figure 1:
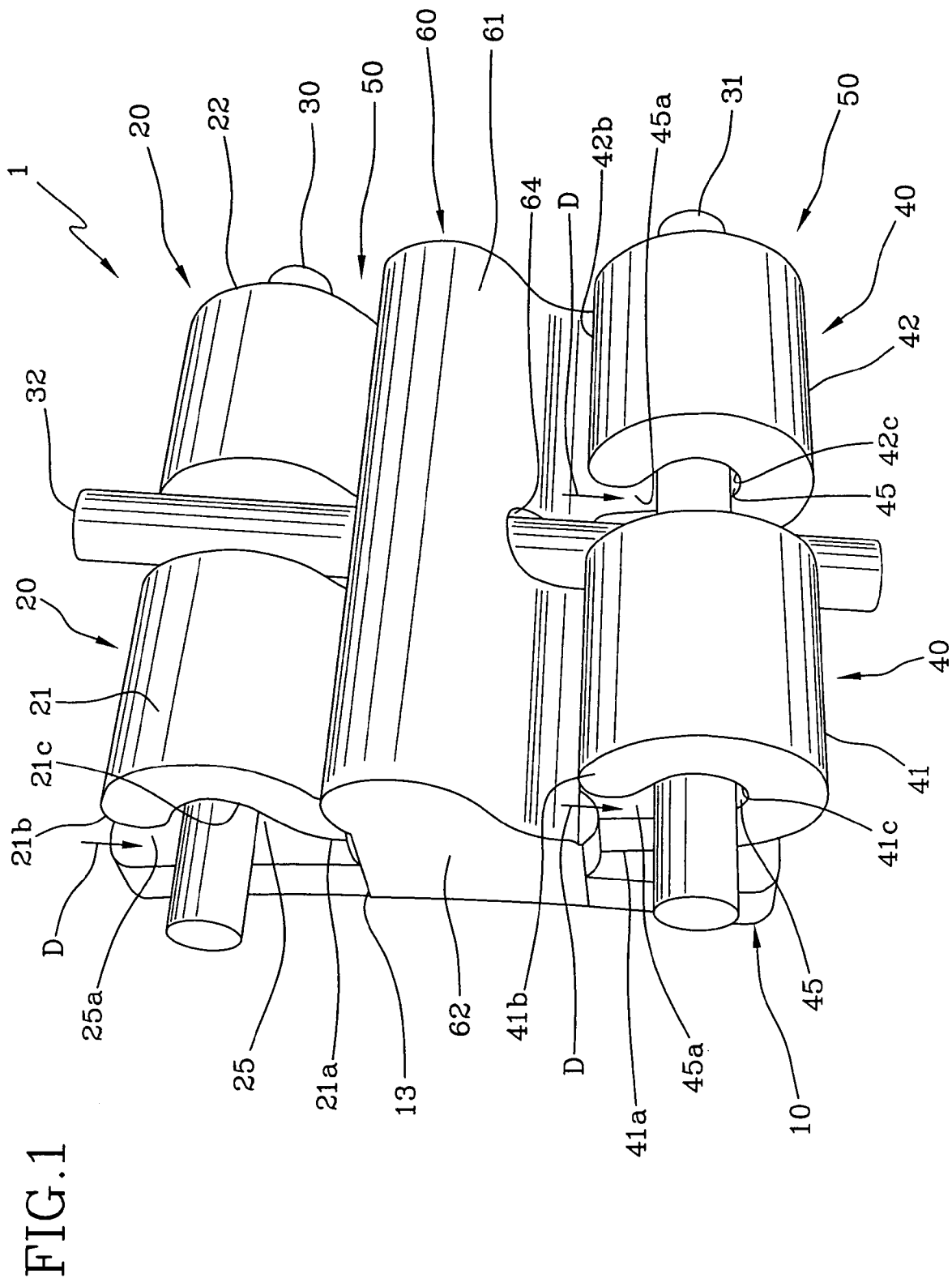
FIG. 1 is a diagrammatic perspective view of a bracket for orthodontic appliances in accordance with the present invention.

With reference to the drawings, a bracket for orthodontic appliances in accordance with the present invention has been generally identified with reference numeral 1.

Bracket 1 first of all comprises a plate-like base 10 (FIGS. 1 and 2) having a preferably square, rectangular or triangular shape; base 10 has a first face 14 set to be fastened to the surface of a tooth through suitable composite materials, and a second face 15 to be used for connection with the other constituent elements of bracket 1.

Mounted on the second face 15 is first support means 20 (FIGS. 1 and 3) defining a first housing 25 for a first archwire 30 in cooperation with the base 10.

In more detail, the first support means 20 comprises a first hook 21 having a first end 21a in contact with the base 10, and a second end 21b suitably spaced apart from said base 10; the first hook 21 further has a concave portion 21c defining part of said first housing 25.

In the preferred embodiment, the first support means 20 further comprises a second hook 22 of a structure quite similar to that of the first hook 21. In fact, the second hook 22 mounted on base 10 in side by side relationship with the first hook 21, has a first end 22a in contact with the base 10 and a second end 22b suitably spaced apart from said base 10.

The second hook 22 also has a concave portion 22c defining the first housing 25 together with the concave portion 21c of the first hook 21 and the base 10 itself.

Practically, the first and second hooks 21, 22 have a substantially C-shaped conformation the concavities of which are in alignment with each other and face the base 10; as the second ends 21b, 22b of the first and second hooks 21, 22 are spaced apart from base 10, an opening 25a in the housing 25 can be obtained.

Through the opening 25a the first archwire 30 can be inserted into the housing 25 in a direction substantially parallel to the planar extension of the base 10 and perpendicular to the longitudinal extension of the first housing 25 itself.

Bracket 1 further comprises second support means 40 mounted on the second face 15 of base 10 for engagement of said base 10 with a second archwire 31; in fact the second support means 40 defines a second housing 45 for the second archwire 31.

In more detail, the second support means 40 comprises at least one first hook 41 having a first end 41a in contact with the base 10 and a second end 41b spaced apart from said base 10; a concave portion 41c of the first hook 41 is part of said second housing 45.

In the preferred embodiment, the second support means 40 is further provided with a second hook 42 having a first end 42a in contact with the base 10 and a second end 42b spaced apart from said base 10; a concave portion 42c of the second hook 42 defines part of the second housing 45.

Practically, the first and second hooks 41, 42 of the second support means 40 are disposed in side by side relationship with each other and have a U-shaped conformation the concavity of which faces the first support means 20; due to the fact that the second ends 41b, 42b are suitably spaced apart from base 10, an opening 45a can be obtained through which the second archwire 31 can be inserted into the second housing 45 in a direction parallel to the planar extension of base 10 and perpendicular to the longitudinal extension of the second housing 45.

Figure 2:
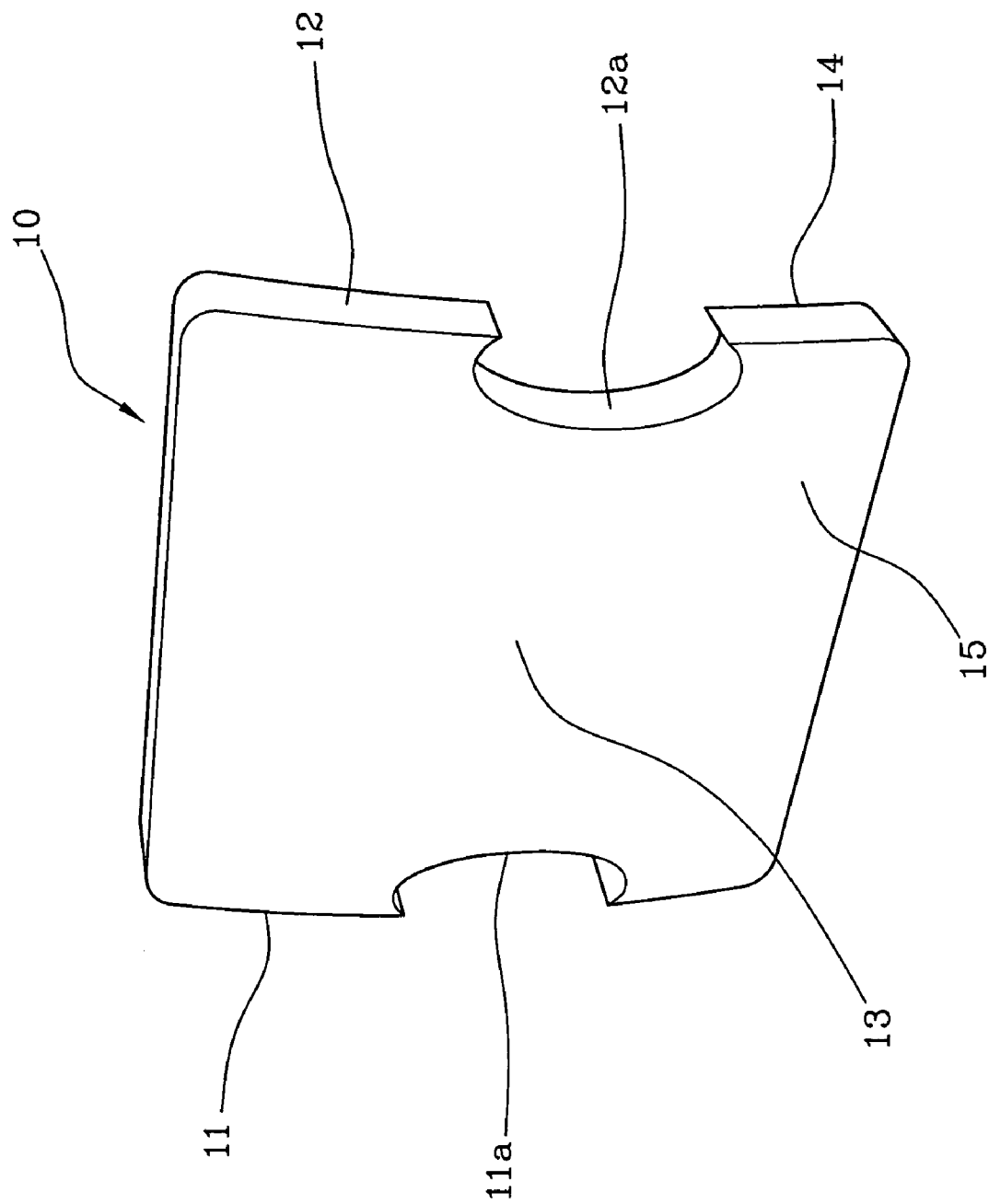
FIGS. 2, 3 and 4 are diagrammatic perspective views of individual elements forming the bracket in FIG. 1.

In other words, by virtue of the above described structure, the first archwire 30 and second archwire 31 are inserted into the first and second housings 25, 45 respectively, along the same insertion direction denoted at D in FIG. 1.

It is to be noted that the base 10 has a median portion 13 interposed between the first and second housings 25, 45; the opening 25a of the first housing is on the opposite side with respect to this median portion 13 whereas the opening 45a of the second housing 45 faces said median portion 13.

Figure 3:
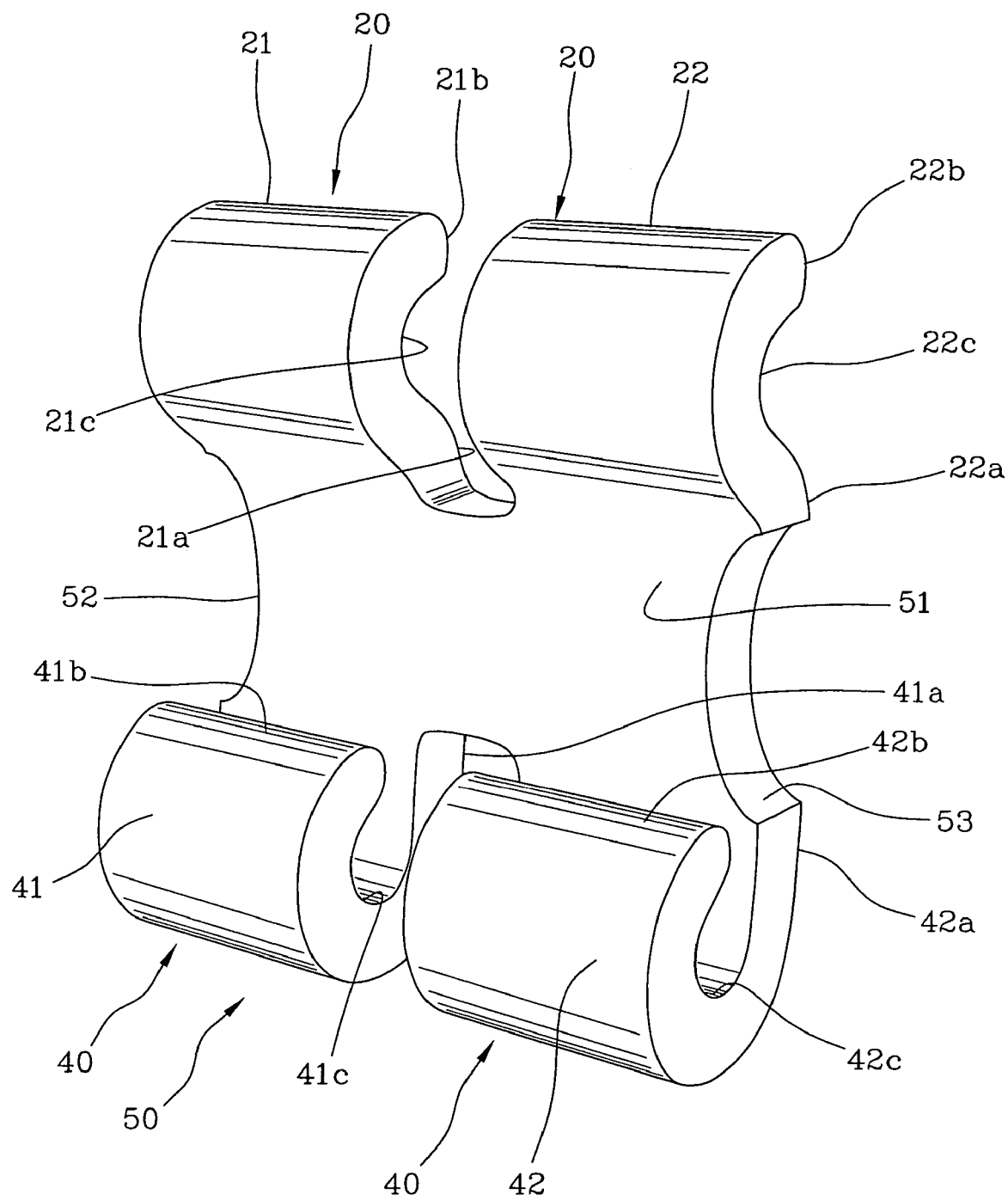

In the preferred embodiment, the first and second support means 20, 40 (i.e. hooks 21, 22, 41, 42) are of one piece construction and form a single supporting body, denoted at 50 in FIGS. 1 and 3.

The archwires 30, 31 are preferably of a circular cross section; correspondingly, the first and second housings 25, 45 suitably conform in shape with said archwires and have a curved inner profile; in particular, the concave portions 21c, 22c, 41c, 42c of hooks 21, 22, 41, 42 seen in cross section with respect to the longitudinal extension of the housings 25, 45, appear as portions of a circumference of a radius equal to or slightly greater than that of the archwires 30, 31.

Due to the above described technical features, one or more moments tending to improve the tooth inclination and orientation can be imposed to a patient's tooth.

In more detail, through inclination of the archwires 30, 31 in a plane parallel to the planar extension of the base 10, a rotation around the vestibulum-lingualis axis can be imposed to the tooth and, through inclination of the archwires 30, 31 in a horizontal plane, the tooth can be given a rotation around a vertical axis.

If a rotation around a meso-distal axis is to be imposed to the tooth, it is sufficient to adjust the mutual position of the two archwires 30, 31.

For example, being assumed that bracket 1 is fastened to the lingual wall of a tooth of the lower dental arch, the first archwire 30 is positioned at the upper tooth end, whereas the second archwire 31 is closer to the lower tooth end.

If the first archwire 30 is such arranged as to impose a force orthogonal to base 10 and directed away therefrom, while the second archwire 31 is such disposed as to exert a parallel force which however has an opposite direction, a tooth rotation tending to move the upper tooth end towards the inside of the oral cavity is obtained.

Vice versa, by arranging the first archwire 30 in such a manner that a force orthogonal to base 10 and directed to the base 10 itself is imposed, while a parallel force which however has an opposite direction is imposed by the second archwire 31, a rotation tending to move the upper tooth end towards the outside of the oral cavity is obtained.

Obviously, a similar speech is also valid when bracket 1 is fastened to a tooth of the upper dental arch; the only difference is that when application to a tooth of the upper arch is carried out, bracket 1 must be overturned with respect to the configuration shown in FIG. 1, so that the first archwire 30 is positioned at the lower tooth end and the second archwire 31 is closer to the upper tooth end.

In other words, bracket 1 is such fastened to the tooth that the first support means 20 is close to the occlusal end of the tooth itself, whereas the second support means 40 is closer to the opposite end.

It is further to be pointed out that bracket 1 can be fastened both to the inner surface and to the outer surface of the tooth, depending on whether a lingual appliance or a vestibular appliance is respectively used.

Figure 4:
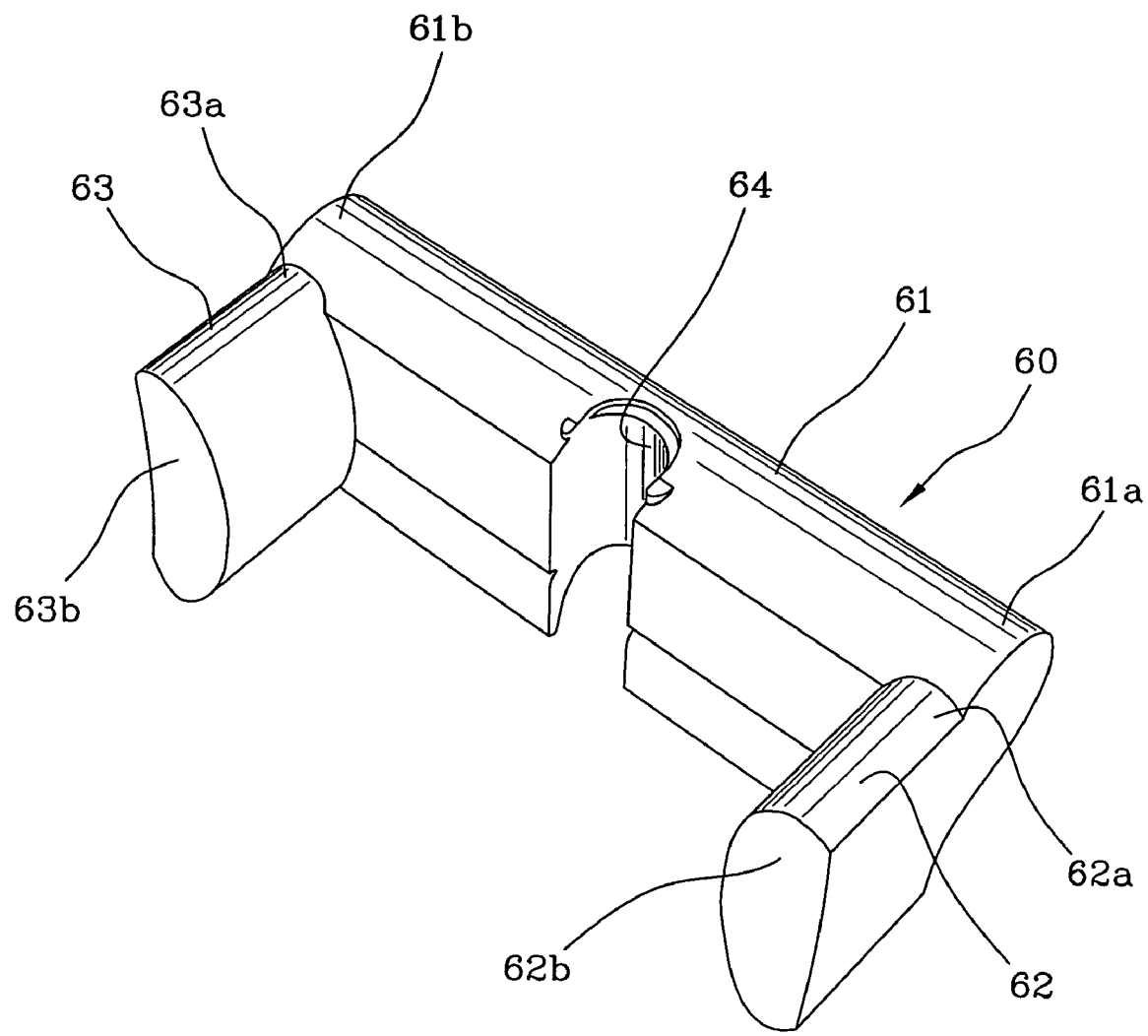

To keep the first and second support means 20, 40 fastened to base 10, bracket 1 further comprises a connecting element 60 (FIGS. 1 and 4); this element has an elongated body 61 with a first and a second end 61a, 61b opposite to each other.

Extending from the first and second ends 61a, 61b respectively, are two wings 62, 63 designed to form a U-shaped element that is positioned on either side of the supporting body 50 to keep the latter in contact with base 10.

In more detail, the wings 62, 63 have a first end 62a, 63a, and a second end 62b, 63b, respectively; the first ends 62a, 63a are fastened to the elongated body 61, at the first and second ends 61a, 61b thereof, respectively.

The second ends 62b, 63b are linked to base 10 at the sides 11, 12; in fact said sides each have a concave portion 11a, 12a, set to house the second end 62b, 63b of a corresponding wing 62, 63.

The fastening link between the wings 62, 63 and base 10 can be obtained by welding, for example.

To facilitate the welding operation and make this link reliable, the base 10 and the connecting element 60 can both be made of a metal material and in particular of stainless steel (the medical steel known as AISI316L, for example) or titanium.

The supporting body 50 too can be made of a metal material, such as stainless steel or titanium; alternatively, for the supporting body 50 a shape-memory metal material can be used, to facilitate insertion of the archwires 30, 31 into the respective housings 25, 45. In particular, a nickel-titanium (NiTi) alloy can be used.

In addition, the supporting body 50 can have a flat portion 51 interposed between the first and second support means 20, 40; when bracket 1 is assembled, the flat portion 51 is maintained in contact with the median portion 13 by means of the elongated body 61. The flat portion 51 has two recesses 52, 53 to allow engagement between the wings 62, 63 and base 10.

In addition to the above, the connecting element 60 has a groove 64; this groove has a longitudinal cross extension which is preferably perpendicular to the longitudinal extension of the housings 25, 45.

The groove 64 defines an auxiliary housing for a pin 32 that is vertically inserted into bracket 1 and the function of which is to force the first archwire 30 against the second face 15 of base 10 and the second archwire 31 against the concave portion 41c, 42c of the hooks 41, 42; in this way, bracket 1 is fastened to the archwires 30, 31 in a very reliable manner and undesirable sliding side actions of bracket 1 relative to the archwires 30, 31 are prevented.

In addition, the vertical pin 32 can be used to support springs, rubber bands and other elements known to those skilled in the art and designed to force side translations of the teeth.

Further portions of the auxiliary housing for pin 32 can also be obtained between the first and second hooks 21, 22 of the first support means 20 and between the first and second hooks 41, 42 of the second support means 40.

It is to be pointed out that the outer surface of hooks 21, 22, 41, 42 and of the elongated body 61 is rounded, so that no trouble is created to the patient who can better endure the orthodontic appliance in the oral cavity.

The outer surface of the elongated body 61 has a convex-concave outline so that the patient's uncomfortableness is minimized and insertion of the second archwire 31 into the second housing 45 is facilitated.

In the light of the above it is apparent that in practical applications bracket 1 is currently used together with a plurality of brackets having a quite similar structure; in fact, an orthodontic appliance comprises first and second archwires 30, 31 preferably having a circular cross section and a predetermined number of brackets.

Each bracket, made as above described, is fastened to a respective one of the patient's teeth and, depending on the position and conformation of the two archwires 30, 31, it imposes predetermined correction forces to the tooth itself.

Figure 5A:
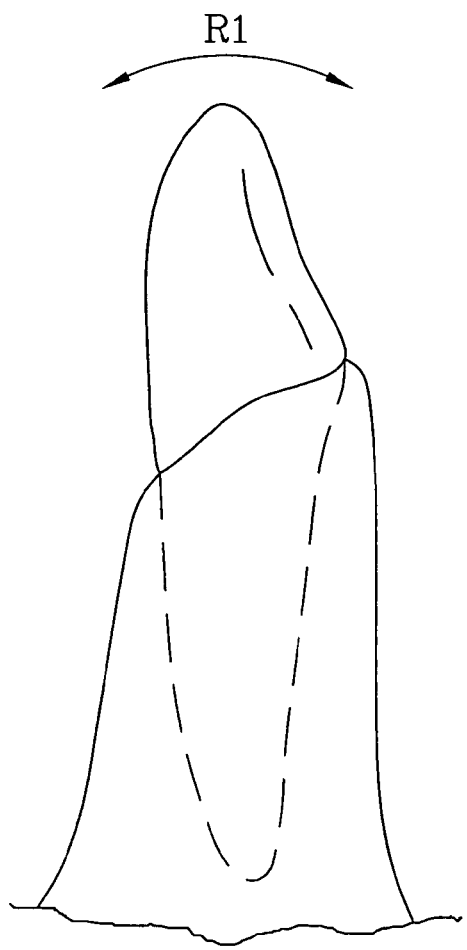
FIGS. 5a, 5b, 5c are diagrammatic side, front and plan views respectively of a tooth to which the bracket shown in FIG. 1 can be applied.
Figure 5B:
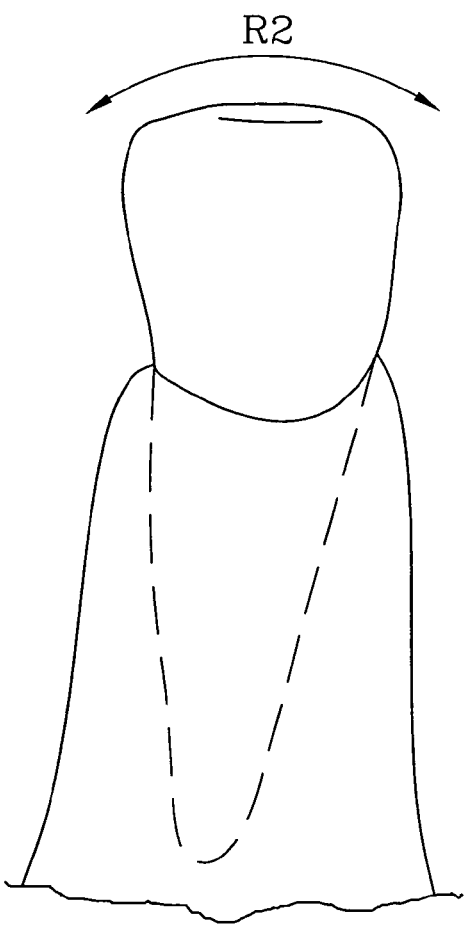
Figure 5C:
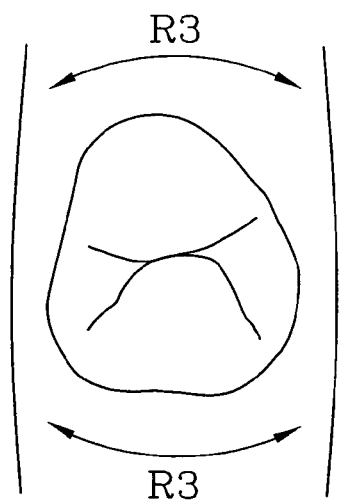

In particular, the following rotations can be imposed:

a rotation around the meso-distal axis (in this connection see FIG. 5a diagrammatically representing a side view of a tooth), identified with R1;

a rotation around the vestibulum-lingualis axis (see FIG. 5b diagrammatically representing a front view of a tooth) identified with R2;

a rotation around the vertical axis (see FIG. 5c diagrammatically representing a plan view of a tooth) identified with R3.

The invention achieves important advantages.

First of all, the bracket in accordance with the invention enables all efforts transmitted to the tooth to be controlled in a precise and reliable manner, in particular with reference to the rotation around the meso-distal axis.

In addition, the effort transmitted by the archwires to the base is not directly applied through the welding spots, but through the mechanical link obtained by means of the above described connecting element; in this manner the bracket structure is particularly safe and strong.

A further advantage is found in the fact that insertion of the archwires into the respective housings is very easy, due to the introduction direction allowed by the bracket structure and the materials used; in addition, the archwire is retained in place without ligatures being required.

Another advantage resides in that the moments applied to the teeth through the above described appliance can be easily corrected and varied even after the appliance has been installed in the patient's oral cavity.

What is claimed is:

1. A bracket for orthodontic appliances comprising:
   a plate-like base (10);
   first support means (20) mounted on said base (10) and defining a first housing (25) for a first archwire (30);
   second support means (40) mounted on said base (10) and defining a second housing (45) for a second archwire (31)
   wherein said first and second support means (20, 40) are of one piece construction and define a single supporting body (50), said bracket further comprising a connecting element (60) to fasten said supporting body (50) to said base (10), wherein said connecting element (60) comprises:
   an elongated body (61) having a first and a second end (61a, 61b) opposite to each other;
   a pair of wings (62, 63) each extending from a respective end (61a, 61b) of said elongated body (61) in a direction transverse to a longitudinal extension of said elongated body (61), said wings (62, 63) being each fastened to said base (10), said supporting body (50) being housed between said wings (62, 63).

2. The bracket as claimed in claim 1, wherein said base (10) has a median portion (13) interposed between said first and second housings (25, 45).

3. The bracket as claimed in claim 2, wherein said first housing (25) has an opening (25a) facing away from said median portion (13).

4. The bracket as claimed in claim 2, wherein said second housing (45) has an opening (45a) facing said median portion (13).

5. The bracket as claimed in claim 1, wherein said first support means (20) comprises at least one first hook (21) having a first end (21a) in contact with said base (10) and a second end (21b) spaced apart from said base (10).

6. The bracket as claimed in claim 5, wherein said first support means (20) further comprises a second hook (22) disposed in side by side relationship with said first hook (21), said second hook (22) having a first end (22a) in contact with said base (10) and a second end (22b) spaced apart from said base (10), concave portions (21c, 22c) of said first and second hooks (21, 22) of the first support means (20) defining said first housing (25).

7. The bracket as claimed in claim 1, wherein said second support means (40) comprises at least one first hook (41) having a first end (41a) in contact with said base (10) and a second end (41b) spaced apart from said base (10).

8. The bracket as claimed in claim 7, wherein said second support means (40) further comprises a second hook (42) disposed in side by side relationship with said first hook (41), said second hook (42) having a first end (42a) in contact with said base (10) and a second end (42b) spaced apart from said base (10), concave portions of said first and second hooks (41, 42) of the second support means (40) defining said second housing (45).

9. The bracket as claimed in claim 1, wherein said base has two opposite sides (11, 12) each provided with a respective concave portion (11a, 12a) to house the wings (62, 63) of said connecting element (60).

10. The bracket as claimed in claim 1, wherein said connecting element (60) has a concave portion (64) provided with a longitudinal extension transverse to a longitudinal extension of said first and second housings (25, 26).

11. The bracket as claimed in claim 1, wherein said base (10) is made of stainless steel.

12. The bracket as claimed in claim 1, wherein said first and second support means (20, 40) are made of a nickel and titanium alloy.

13. The bracket as claimed in claim 1, wherein said connecting element (60) is made of stainless steel.

14. A bracket for orthodontic appliances, comprising:
- a plate-like base (10), having at least two opposite sides (11, 12) each provided with a respective concave portion (11a, 12a);
- a supporting body (50) of one piece construction, having first support means (20) and second support means (40) defining a first housing (25) for a first archwire (30) and a second housing (45) for a second archwire (31) respectively, said base (10) having a median portion (13) interposed between said first and second housings (25, 45), said first housing (25) being provided with an opening (25a) on the opposite side with respect to said median portion (13), said second housing (45) being provided with an opening (45a) facing said median portion (13);
- a connecting element (60) having an elongated body (61) with a first and a second end (61a, 61b) opposite to each other and a pair of wings (62, 63) extending each from a respective end (61a, 61b) of said elongated body (61) in a direction transverse to a longitudinal extension of said elongated body (61), said wings (62, 63) being each fastened to said base (10), said supporting body (50) being housed between said wings (62, 63).

15. An orthodontic appliance comprising:
- a first archwire (30);
- a second archwire (31);
- at least one bracket (1) having a plate-like base (10), first support means (20) mounted on said base (10) and defining a first housing (25) for said first archwire (30), and second support means (40) mounted on said base (10) and defining a second housing (45) for said second archwire (31)

wherein said first and second support means (20, 40) are of one piece construction and define a single supporting body (50), said bracket further comprising a connecting element (60) to fasten said supporting body (50) to said base (10), wherein said connecting element (60) comprises:
- an elongated body (61) having a first and a second end (61a, 61b) opposite to each other;
- a pair of wings (62, 63) each extending from a respective end (61a, 61b) of said elongated body (61) in a direction transverse to a longitudinal extension of said elongated body (61), said wings (62, 63) being each fastened to said base (10), said supporting body (50) being housed between said wings (62, 63).

16. The orthodontic appliance as claimed in claim 15, wherein said bracket (1) further has a concave portion (64) having a longitudinal extension transverse to a longitudinal extension of said first and second housings (25, 45).

17. The orthodontic appliance as claimed in claim 16, further comprising a pin (32) housed in said concave portion (64) and disposed transversely of said first and second archwires (30, 31).

* * * * *